(12) United States Patent
Behar-Cohen

(10) Patent No.: US 9,962,287 B2
(45) Date of Patent: May 8, 2018

(54) DEVICE FOR THE TREATMENT OF AN OCULAR DISEASE

(75) Inventor: Francine Behar-Cohen, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 735 days.

(21) Appl. No.: 14/238,949

(22) PCT Filed: Aug. 14, 2012

(86) PCT No.: PCT/IB2012/054146
§ 371 (c)(1),
(2), (4) Date: Jul. 14, 2014

(87) PCT Pub. No.: WO2013/024437
PCT Pub. Date: Feb. 21, 2013

(65) Prior Publication Data
US 2014/0316372 A1    Oct. 23, 2014

(30) Foreign Application Priority Data

Aug. 16, 2011  (EP) ..................................... 11177640

(51) Int. Cl.
*A61F 9/00* (2006.01)
*A61N 1/05* (2006.01)
*A61N 1/32* (2006.01)
(52) U.S. Cl.
CPC .......... *A61F 9/0008* (2013.01); *A61N 1/0526* (2013.01); *A61N 1/327* (2013.01)
(58) Field of Classification Search
CPC .. A61N 1/0492; A61N 1/0448; A61N 1/0468; A61N 1/0488; A61N 1/0526; A61N 1/327; A61F 9/0008
See application file for complete search history.

(56) References Cited

U.S. PATENT DOCUMENTS

2003/0236484 A1* 12/2003 Lynch ................. A61F 9/00781
604/8
2008/0183123 A1* 7/2008 Behar-Cohen ......... C12N 15/87
604/21
(Continued)

FOREIGN PATENT DOCUMENTS

FR      2 928 536 A1    9/2009
WO    2006/123248 A2   11/2006
WO    2008/013913 A2    1/2008

OTHER PUBLICATIONS

Olsen et al., "Cannulation of the Suprachoroidal Space: A Novel Drug Delivery Methodology to the Posterior Segment", American Journal of Ophthalmology, Nov. 1, 2006, pp. 777-787, vol. 142, No. 5, Ophthalmic Publ., Chicago, IL.
(Continued)

*Primary Examiner* — Bhisma Mehta
*Assistant Examiner* — Hamza Darb
(74) *Attorney, Agent, or Firm* — Whitham, Curtis & Cook, P.C.

(57) ABSTRACT

An electrode device having an insertion part (12) adapted to be inserted into the suprachoroidal space of an eye so as to reach a service position, and an handling part (14) for manipulation of the electrode device, said electrode device comprising: —a support (25) having a distal part (31); —a set of wires (20) supported by said support and mobile between a retracted position in which said wires substantially extend along the support, and a deployed position in which respective parts of said wires, called "outside parts", project from said distal part (31) of the support; —an electrically conductive element forming at least a portion of a said outside part or supported by a said outside part; —an electrical conductor (60) enabling, in said deployed position, an electrical connection between said electrically conductive element and an electrical generator; and —an actuator (16, (Continued)

60) adapted for an operator to move the set of wires from said retracted position to said deployed position in said service position.

16 Claims, 5 Drawing Sheets

(56) References Cited

U.S. PATENT DOCUMENTS

| | | | | |
|---|---|---|---|---|
| 2009/0254019 A1* | 10/2009 | Gehl | ................ | A61B 18/1477 |
| | | | | 604/21 |
| 2009/0281477 A1* | 11/2009 | Mikus | ................ | A61B 18/1477 |
| | | | | 604/21 |
| 2011/0152749 A1* | 6/2011 | Touchard | .............. | A61F 9/0017 |
| | | | | 604/21 |
| 2011/0238057 A1* | 9/2011 | Moss | ................ | A61B 18/1477 |
| | | | | 606/33 |

OTHER PUBLICATIONS

El Sanharawi, "Protein delivery for retinal diseases: from basic considerations to clinical applications", Progress in Retinal and Eye Research, Nov. 1, 2010, pp. 443-465, vol. 29, No. 6.

* cited by examiner

DEVICE FOR THE TREATMENT OF AN OCULAR DISEASE

FIELD OF THE INVENTION

The present invention relates to an electrode device for the treatment of an ocular disease in a subject.

BACKGROUND OF THE INVENTION

In recent years, there have been exciting new advances for the treatment of ocular diseases such as age-related macular degeneration and diabetic retinopathy, using biotherapies. Because the eye is a small, confined organ, isolated by barriers, it has been identified as an organ of choice for local gene therapy.

For example, hereditary retinal dystrophies are due to mutations in genes encoding proteins in photoreceptors (cones and rods), or in retinal pigment epithelial cells (RPE). Whilst gene replacement in photoreceptor cells is still under pre clinical evaluation, the most striking advances in this field have been made for RPE65 gene replacement in RPE cells, for the treatment of Leber congenital amaurosis (LCA). Not only was it shown that viral gene transfer in the RPE was feasible and efficient in animal models, but recently, patients have received the sub retinal injection of rAAV4 with promising functional results, giving real hopes for patients suffering from blinding diseases.

Viral vectors allow efficient transfection of RPE cells and have serve to validated proof of concepts, but the long-term persistence of viral particles in the retina and the brain continues to raise safety concerns, particularly when treatment is being applied in young children.

When injected into the vitreous, viral vectors do not reach the RPE cells and only their sub-retinal injection was shown effective for targeting RPE cells or photoreceptors. Moreover, using the sub retinal injection, RPE cells are only transfected in, and at the vicinity of the detached retina area, which implies detaching the macula when central vision recovery is targeted. Such a macular detachment may be associated with a threat to vision. Indeed, it is well known that poor vision recovery after retinal detachment is correlated with macular detachment. Recent work using spectral domain OCT has brought evidence that following successful surgical treatment of retinal detachment, 62% of the eyes presented anatomical foveal abnormalities, and that particularly, external limiting membrane disruption, observed only when the macula was detached before surgery, was associated with the worst prognosis for vision. Even if controversies still exist regarding the factors that may predict vision recovery after macular detachment, the health of the macula at the time of reattachment is probably the most critical variable. In diseased eyes, knowing the uncertainty of central vision recovery after macular detachment, it is difficult to ensure that submacular injection is not risky.

Many non-viral gene transfer vectors or methods have been developed and adapted for ocular gene therapy (Andrieu-Soler C Mol Vis 2006 12:1334; Bejjani R A Surv Ophthalmol 2007 52:196; Bloquel C Adv Drug Deliv Rev 2006 58:1224). Among those, electroporation, also called "electrotansfer" when the current drives plasmid DNA into cells, is among the most efficient ones ((Mir L M Adv Genet 2005 54:83; Mir L M Methods Mol Biol 2008 423:3; Isaka Y Expert Opin Drug Deliv 2007 4:561) and has been developed up to clinical evaluation (Daud A I J Clin Oncol 2008 26:5896). Previous reports have shown that after sub retinal administration of the plasmids, electroporation allowed the efficient transfection of new-born murine RPE (Matsuda T Proc Natl Acad Sci USA 2004 101:16) and delayed retinal degeneration in animal models (Chen B Science 2009 323:256). Efficient and prolonged RPE transfection was also achieved in the adult rat using a combination of sub retinal plasmids injection containing specific RPE promoter and electroporation (Kachi S Gene Ther 2005 12:843; Johnson C J Mol Vis 2008 14:2211).

WO 2006/123248 describes a device for delivering a therapeutic product to the ocular sphere.

The suprachoroidal space is a potential space in the eye that is located between the choroid, which is the inner vascular tunic, and the sclera, the outer layer of the eye. The suprachoroidal space extends from the anterior portion of the eye posterior to the ciliary body to the posterior end of the eye up to the optic nerve. The suprachoroidal space of the eye has been thus studied as a possible route for drug delivery. See, e.g., Olsen, et al., American J. Opthamology 142(5): 777-87 (November 2006); PCT Patent Application Publication No. WO 2007/100745 to Iscience Interventional Corporation. The suprachoroidal space may indeed provide a potential route of access from the anterior region of the eye to treat the posterior region. However said route has not been envisaged for non viral gene therapy.

There is a need for an efficient electroporation device which may be used to transfer an agent contained in a pharmaceutical composition introduced in the suprachoroidal space.

It is an object of the invention to provide such a device.

SUMMARY OF THE INVENTION

The invention concerns an electrode device having an insertion part adapted to be inserted into the suprachoroidal space of an eye so as to reach a service position, and an handling part for manipulation of the electrode device, said electrode device comprising:
  a support having a distal part;
  a set of wires supported by said support and mobile between a retracted position in which said wires substantially extend along the support, and a deployed position in which respective parts of said wires, called "outside parts", project from said distal part of the support;
  an electrically conductive element forming at least a portion of a said outside part or supported by a said outside part;
  an electrical conductor enabling, in said deployed position, an electrical connection between said electrically conductive element and an electrical generator; and
  an actuator adapted for an operator to move the set of wires from said refracted position to said deployed position in said service position.

As will emerge in more details hereinafter, it is therefore possible to insert through a mini-incision and between the choroid and the sclera, the insertion part of the electrode device according to the invention, to deploy the set of wires so as to create a large area electrode, and to generate, with the help of a counter electrode, in particular a surface electrode, and of an electrical generator, an electrical field efficient for electroporation. Preferably, a device according to the invention comprises one or more of the following optional characteristics:
  The set of wires may comprise 2, 3, 4, 5, 6, 7, 8, 9 or more wires, and/or preferably, less than 20, preferably less than 15 wires;

Each of a plurality of said outside parts of said wires, preferably each of said outside parts, comprises a respective electrically conductive element, the electrical conductor enabling, in said deployed position, an electrical connection between said electrically conductive elements and said electrical generator;

The electrically conductive element of a wire is constituted by the outside part of said wire, or by said wire, and/or by an electrically conductive coating of said outside part and/or by an electrically conductive web at least partially supported by said outside part;

More than 2, 3, 4, 5, 6, 7, 8, 9 or more of said outside parts, preferably all of said outside parts comprise a respective electrically conductive element;

Each of said outside parts, preferably each of said wires, is made of an electrically conductive material, preferably in a conductive non oxidative metal, preferably selected from iridium, platinum, iridium/platinum, and gold, or made of carbon, The insertion part of the electrode device is curved. The radius of curvature is preferably greater than 9 mm, 10 mm or 11 mm, and/or less than 15 mm, less than 14 mm, less than 13 mm, or less than 12 mm;

The width and/or the thickness of the insertion part of the electrode device is less than 2.0 mm, less than 1.5 mm, less than 1.2 mm, less than 1.0 mm, less than 0.8 mm, or less than 0.5 mm;

The distal part of the support is provided with a lumen which laterally diverges at the approach of a distal end of the support and opens outwardly at said distal end and/or divides (or splits) into a plurality of guiding tubes opening outwardly through respective openings, said lumen and said guiding tubes containing, in the retracted position, one or several of said wires;

The diameter of the wires is more than 0.01 mm, more than 0.05 mm and/or less than 1 mm, less than 0.5 mm, less than 0.3 mm, or less than 0.2 mm;

The length of said outside parts is more than 1 mm, more than 3 mm, more than 4 mm and/or less than 15 mm, less than 12 mm, less than 10 mm, less than 8 mm, less than 6 mm (for each of said outside parts);

The wires are elastic;

In the deployed position, the outside parts of the wires have a curved shape;

In the deployed position, said outside parts extend along a spherical surface. The radius of curvature of this spherical surface is preferably greater than 9 mm, 10 mm or 11 mm, and/or less than 15 mm, less than 14 mm, less than 13 mm, or less than 12 mm;

In said deployed position, at least one of said wires projects from said support in the shape of a loop;

The convex surface defined by the outside parts of the wires is more than $10.10^{-6}$ m$^2$, more than $15.10^{-6}$ m$^2$, more than $20.10^{-6}$ m$^2$, more than $30.10^{-6}$ m$^2$, and/or less than $50.10^{-6}$ m$^2$;

The device comprises a cable which, in the service position, is able to:
establish, at least in the deployed position, an electrically conductive path between said electrically conductive element(s); and/or
establish a mechanical relationship between the set of wires and the outside of the eye so that an operator may move said set of wires from the retracted position to the deployed position;

The device comprises an optical guide enabling, in the service position, the illumination of at least a part of the distal part of the device, in particular the illumination of its distal end.

In an embodiment, the support is a sleeve, slidably mounted on a cable, so that a pull or a push on the support makes the wires exit from or enter into the support.

The invention also concerns an electroporation device comprising an electrode device according to the invention, a counter electrode and an electrical generator so as to polarize differently said electrically conductive element(s) of said wires of the electrode device according to the invention and the counter electrode, and adapted so as to generate an electrical field enabling electroporation.

The invention also concerns the use of an electroporation device according to the invention for the electroporation of a therapeutic nucleic acid after delivering a pharmaceutical composition formulated with said therapeutic nucleic acid into the suprachoroidal space of a diseased eye.

Definitions

For illustrative purpose only, "upper", "lower", "horizontal" and "vertical" are defined according to the vertical direction V represented on FIG. 2. Of course, the electrode device may be used in other positions.

"Transversal" means perpendicular to the longitudinal direction (axis Y-Y).

The "service position" is the position of the electrode device in which the distal tip of the electrode device has reached an appropriate location, inside the suprachoroidal space, for the electroporation.

The "convex surface" defined by the outside parts of the wires is the surface of the convex envelope of these outside parts. The "convex envelope" is the convex, closed line, having a minimum length and containing all said outside parts. It may be compared to the region which would be delimited by a rubber band exclusively resting on these outside parts. A convex surface X is represented, for instance, in FIGS. 7 and 9.

Analogous or similar elements may be designated with the same reference. Indicia may be used to distinguish different but similar elements in the same drawing, for instance $38_1$ and $38_2$. The same reference without indicia, for instance 38, is used to designate any of these elements.

"Comprising" means "comprising at least one", unless otherwise described.

BRIEF DESCRIPTION OF THE FIGURES

All the features and advantages of the present invention will become apparent on reading the following description and examining the accompanying drawings, in which.

DETAILED DESCRIPTION

The inventors have evaluated whether the suprachoroidal injection of a plasmid solution in the rat eye, associated with electroporation, could be efficient for the transfection of the choroid and the RPE cells and/or the neuroretina. They bring the proof of concept that using this minimally invasive technique, that does not require sub retinal injection and subsequent detachment, not only RPE cells and choroidal cells, but also photoreceptors are efficiently transfected. Such a method may be used for the treatment of an ocular disease in a subject, in particular with the help of an electroporation device according to the invention.

Electrode Device

Figure 1:
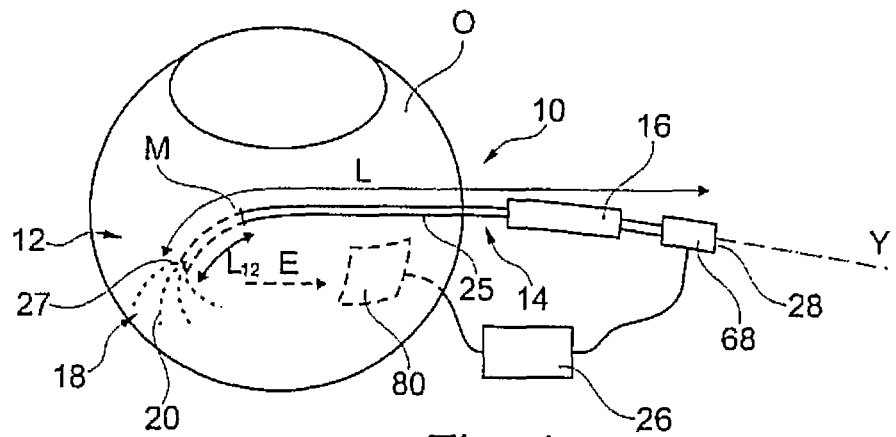
FIG. 1 shows an electrode device according to the invention in a service position, the set of flexible wires being in the deployed position.

An electrode device 10 according to the invention, represented in FIG. 1, comprises an insertion part 12 and a handling part 14. The insertion part 12 is the part of the electrode device which is to be inserted into the suprachoroidal space by the physician. The handling part 14 is the part of the electrode device which is manipulated by the physician to operate the electrode device, in particular to insert the insertion part 12 into the suprachoroidal space and to deploy and retract the set of wires.

In a service position, the insertion part 12 is inserted between the sclera S and the choroid H of an eye. This space is called "suprachoroidal space" I.

The electrode device 10 comprises a set 18 of wires 20, movable, in particular in the service position, from a retracted position to a deployed position, and, preferably, reversely. The electrode device 10 also comprises a support 25 to support and guide said wires 20. The insertion part 12 is adapted for an insertion into the suprachoroidal space in the retracted position.

The electrode device also comprises an actuator intended for an operator to change the position of the set of wires, and an electrical conductor intended to enable the establishment of an electrical connection of the wires 20 with an electrical generator 26.

The length L of the electrode device, in the retracted position, is preferably more than 5 cm, more than 8 cm and/or less than 20 cm, less than 15 cm or even less than 10 cm.

The insertion part 12 of the electrode device is preferably curved, so as to conform to the outside surface of the choroid H.

Figure 2:
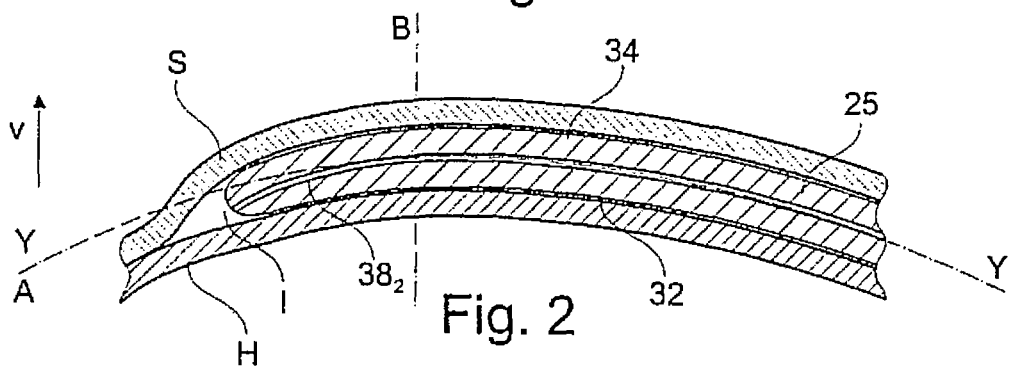
FIG. 2, shows the insertion part of the electrode device of FIG. 1 in a vertical longitudinal median cross section according to plane C, in the retracted position.
Figure 4A:
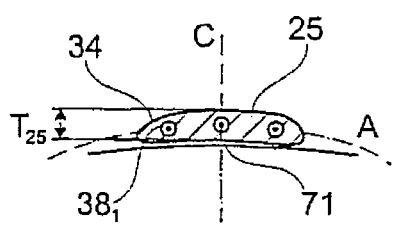
FIGS. 4a to 4c represent transversal cross sections according to plane B, according to different embodiments of the electrode device of FIG. 2.
Figure 4B:
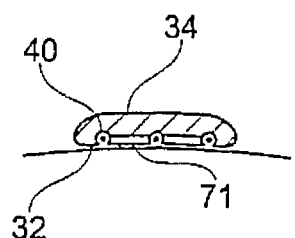
Figure 4C:
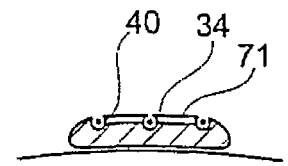

As it may be seen from FIGS. 2 and 4, the bottom outer surface 32 of the insertion part 12 is preferably curved longitudinally (see FIG. 2) and laterally (see FIGS. 4a to 4c) to substantially conform to the curved shape of the choroid H. In the same way, the upper outer surface 34 of the insertion part is preferably curved, both longitudinally and laterally, to substantially conform to the curved shape of the sclera S. Preferably, these surfaces are therefore curved spherically. The radius of curvature of these surfaces is preferably greater than 9 mm, 10 mm or 11 mm, and/or less than 15 mm, less than 14 mm, less than 13 mm, or less than 12 mm.

The transversal cross section of the insertion part 12 may have a circular or, preferably, flat contour, as represented in FIGS. 4a to 4c. To enable minimally invasive surgical access within the suprachoroidal space I, the width $W_{25}$ and/or the thickness $T_{25}$ of the insertion part 12 is preferably less than 2.0 mm, less than 1.5 mm, less than 1.2 mm, less than 1.0 mm, less than 0.8 mm, less than 0.5 mm.

The insertion part 12 of the electrode device has preferably, in the retracted position, a flexible rigidity defined by a flexible modulus equal to or less than about $5.2 \cdot 0.10^{-9}$ kN/m$^2$, preferably less than $4 \cdot 0.10^{-9}$ kN/m$^2$, less than $3 \cdot 0.10^{-9}$ kN/m$^2$, less than $2 \cdot 0.10^{-9}$ kN/m$^2$, less than $1.0 \cdot 0.10^{-9}$ kN/m$^2$. The flexibility of the insertion part 12 enables it to conform to the anatomy of the sclera and choroid as it is pushed into the service position.

The insertion part 12 preferably has a distal tip 30 conformed so as to be atraumatic. The tip 30 is preferably rounded off to achieve a smooth curved surface. Preferably, it is tapered in thickness toward the tip 30 so as to be well suited to opening up the cleavage plane between the sclera S and the choroid H as the insertion part is pushed into the service position. Preferably, the distal tip 30 is not sharp, so that the electrode device of the invention is not configured to be used as a needle.

Moreover, preferably, the outer surface of the insertion part 12 is covered, at least partially, preferably completely, by a lubricious outer coating.

To limit its introduction in the suprachoroidal space, the electrode device may be provided with abutment means (not shown).

Support

In the represented embodiment, the support 25 extends, along its longitudinal axis Y-Y, from the distal tip 30 to the proximal end 28 of the electrode device.

Preferably, the shape of the insertion part 12 is provided by a distal part 31 of the support 25, the distal end of the support corresponding to the distal tip 30 of the electrode device.

The shape of the distal part 31 of the support 25, i.e. its outer surface, is adapted so that, in the retracted position, said distal part may be inserted into the suprachoroidal space of an eye.

In a preferred embodiment, the support 25, and in particular its distal part 31, is tubular along more than 50%, more than 80%, more than 90% or even 100% of its length L.

Preferably, it is provided with a lumen 36 which preferably laterally diverges at the approach to the tip 30. In particular, the transversal dimension of the lumen may increase, for instance so that the divergence of the lumen be in the shape of a section of a cone or of a nozzle (see FIGS. 15, 16a and 16b). The lumen 36 may also radiate into a plurality of guiding tubes 38 opening outwardly through respective openings 40.

The guiding tubes 38 preferably open outwardly laterally (38$_1$) and/or axially (38$_2$). As represented in FIG. 2, the guiding tubes 38 may be oriented so as to guide wires 20 upwardly or downwardly toward the surface of the choroid or of the sclera.

Each guiding tube may contain, in the retracted position, one or several wires 20.

In one embodiment, all the wires exit out of the same opening. The width $W_{25}$ of the support may therefore be very small.

The support 25 may be provided with, or constitute an optical guide, so that light may be transmitted, in particular in the service position, from the outside of the eye to the insertion part 12, and in particular to the distal tip 30. Advantageously, the determination of the location of the insertion part 12 is made easier. An optical fibre may also be fixed on the support 25 to constitute said optical guide.

As it is represented in FIGS. 4b and 4c, some, or all of the guiding tubes 38 may be replaced, at least in part, by grooves 40. The grooves 40 may be practiced in the outer bottom surface 32 (FIG. 4b) or in the outer upper surface 34 (FIG. 4c). The creation of grooves advantageously enables a very low thickness $T_{25}$ for the support 25.

Set of Flexible Wires

The set of wires may comprise 2, 3, 4, 5, 6, 7, 8, 9 or more wires. Preferably, the number of wires is 20 or less, preferably 15 or less.

Each of the wires 20 comprises a respective outside part 64 which, in the deployed position, protrudes, i.e. extends away from the support 25. In the preferred embodiment, each of said outside parts comprises an electrically conductive element. In particular, the electrically conductive element of a wire may be said outside part itself, or said wire itself, or a coating applied on a wire core. The electrically conductive element of a wire is preferably made of a conductive non oxidative metal selected from iridium, platinum, iridium/platinum, and gold, or made of carbon, stainless steel, silver, aluminium, tungsten . . . .

The diameter of any wire 20 is preferably more than 0.01 mm and less than 0.3 mm, preferably less than 0.1 mm.

Preferably, the wires 20 are elastic, in particular may have a shape memory so that, in the deployed position, they may have the desired configuration, as it is described hereafter.

Each wire 20 has preferably, at its free distal end, a plug 52, for instance in silicone, so as to be atraumatic.

At the opposite proximal end 54, the wires 20 are regrouped so as to minimize their bulkiness, and reduce the outer dimensions of the support 25.

Retracted Position

Preferably, more than 80%, more than 90%, more than 95%, preferably 100% of the length of the wires 20 is inside the support 25 in the retracted position. Preferably, the free distal ends of the wires are at less than 1 mm, or less than 0.5 mm of the opening(s) through which they may exit to reach the deployed position.

In the retracted position, the free distal ends of the wires 20 may partially define the outer surface of the electrode device.

Deployed Position

The length of the outside parts 64 is preferably more than 1 mm, more than 3 mm, more than 4 mm and/or less than 15 mm, less than 12 mm, less than 10 mm, less than 8 mm, or less than 6 mm.

In the deployed position, the outside parts of the wires 20 may all have the same length or the lengths may differ.

Preferably, outside parts of wires 20 recover, preferably because of their elasticity, a curved shape so that they extend along a spherical surface, the radius of curvature of which being preferably greater than 9 mm, 10 mm or 11 mm, and/or less than 15 mm, less than 14 mm, less than 13 mm, or less than 12 mm, corresponding to that of the interface between the sclera and the choroid.

In an embodiment, the guiding tubes 38 contribute to the shape of the outside parts of the wires 20.

Preferably, the convex surface defined by the outside parts of the wires 20 is more than $10.10^{-6}$ m$^2$, more than $15.10^{-6}$ m$^2$, more than $20.10^{-6}$ m$^2$, more than $30.10^{-6}$ m$^2$, and/or less than $50.10^{-6}$ m$^2$.

Figure 7:
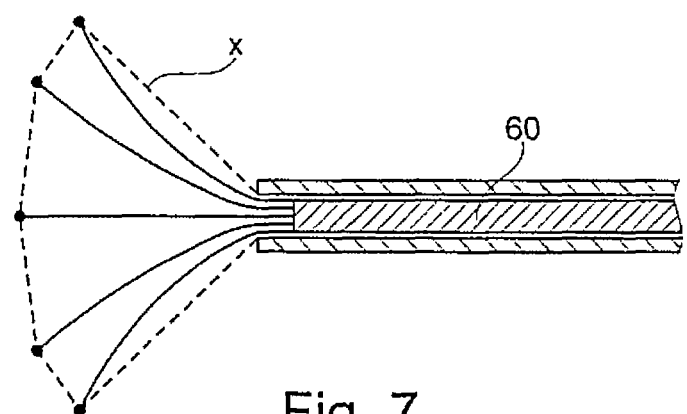
Figure 11:
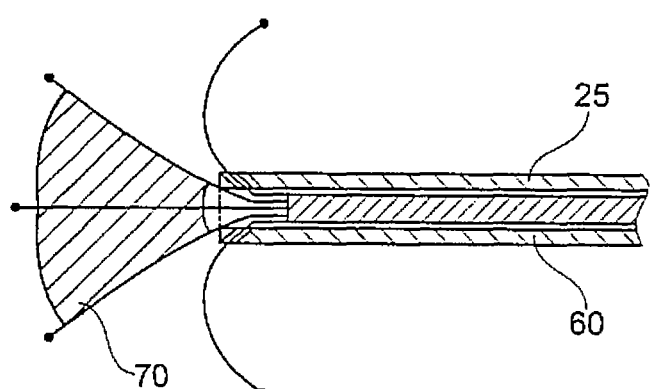

Preferably, all the outside parts of the wires 20 stem from the distal part of the support 25. Some of them, as represented in FIGS. 5, 9, 12, 13 and 14, or all of them, as represented in FIGS. 7 and 11, may extend beyond the tip 30 of the support 25.

They may project from the support 25 symmetrically to the longitudinal axis Y-Y, or symmetrically to the vertical longitudinal median plane C of the support 25, or not. They may radiate or not.

Actuator

Figure 3:
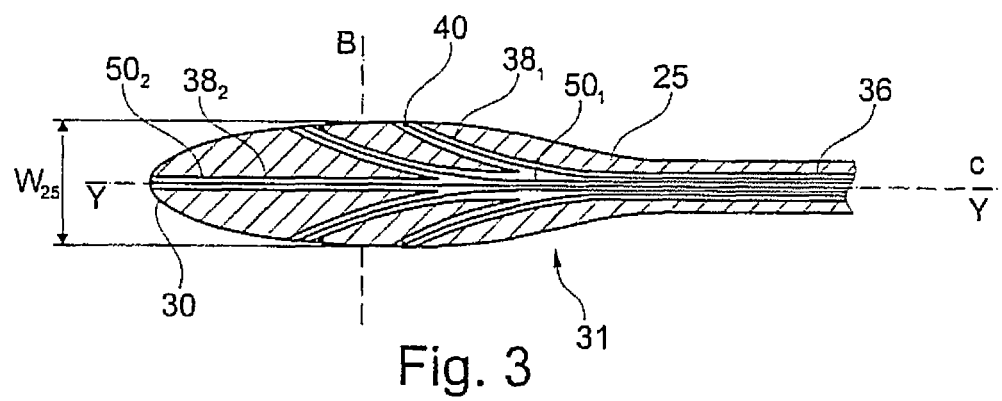
FIG. 3 is a view, in a substantially horizontal longitudinal median cross section according to the curved plane A, of the insertion part of the electrode device of FIG. 2, in the retracted position.
Figure 5:
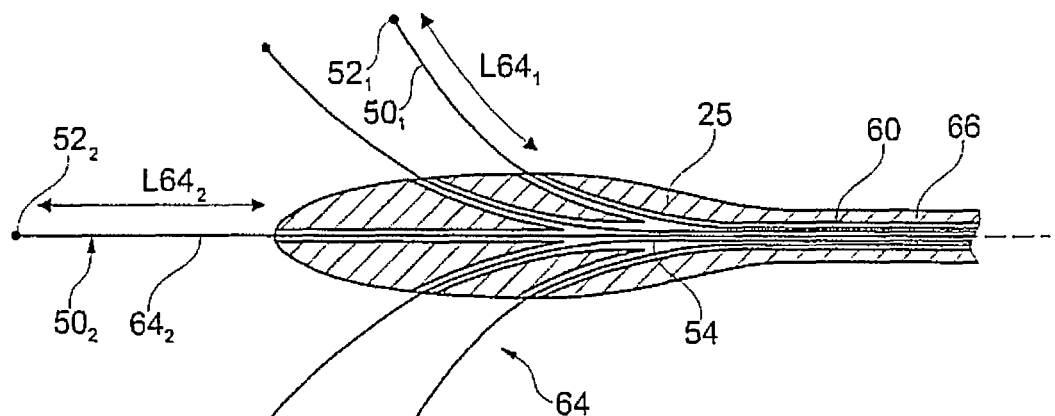
FIG. 5 shows the cross section of FIG. 3 in the deployed position.

The actuator is used to move the set of wires 20 from the retracted position (FIG. 3) to the deployed position (FIG. 5). The actuator may comprise the control handle 16 and a cable 60 which establishes a mechanical relationship between the set of wires and the control handle 16.

Figure 15:
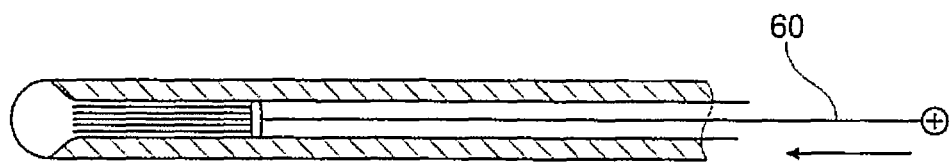
FIG. 15 illustrates an example of deployment of the wires of an electrode device according to the invention.
Figure 15:
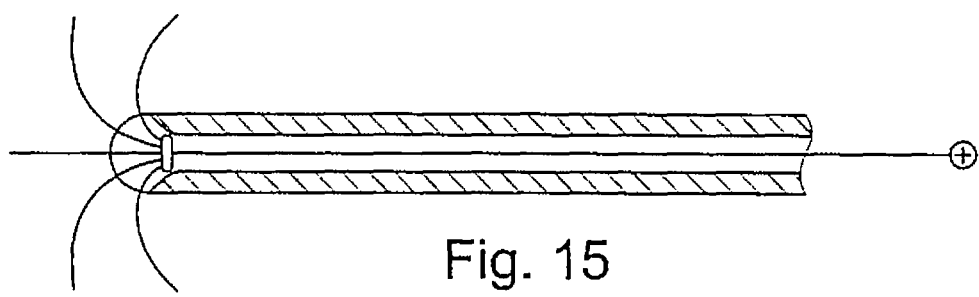
Figure 16A:
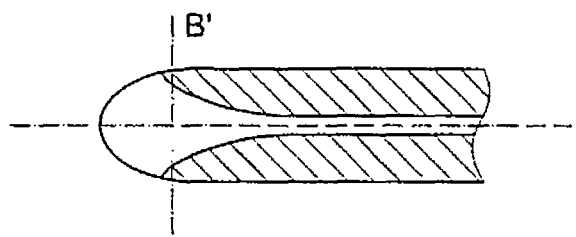
FIGS. 16a and 16b show, in a substantially horizontal longitudinal median cross section according to the curved plane A' and in a transversal cross section according to plane B', respectively, the support of the electrode device of FIG. 15.
Figure 16B:

In particular, the support 25 may be tubular and the cable 60, attached to the proximal ends 54 of the wires, may exit from the proximal part of the support, so that an operator may push or pull the cable in the service position (see FIG. 15). In this embodiment, the cable 60 may slide inside the lumen of the tubular support 25, axially, so as to push or pull the set of wires, and move said wires from the deployed position to the retracted position.

In one embodiment, the control handle 16 may be slidably mounted on the support 25 and be fixed onto the cable 60, for instance through a longitudinal slot of the support 25.

The cable 60 may comprise, or even be formed by the wires 20. Advantageously, the cable can therefore be part of the electrical conductor which is described hereafter. In this embodiment in particular, it preferably comprises a sheath 66 maintaining the wires together, like an electrical multistrand cable. The cable 60 may also not comprise the wires 20.

Electrical Conductor

The electrical conductor is used to establish, at least in the deployed position, an electrically conductive path between the electrically conductive elements of the outside parts of the wires and a terminal 68 to be connected to an electrical generator.

Preferably, the cable 60 of the actuator enables an electrical connection of the wires 20 with the terminal 68. In particular when the cable 60 does not comprise any of the wires 20, it may be made of an electrically conductive material, or be coated with an electrically conductive material extending so as to enable the conduction of electrical current from the terminal 68 to the wires 20.

The electrical conductor may also be supported by the support 25. In particular, it may be the support itself or a part of the support, or an electrically conductive layer covering, at least partially, the surface of the lumen 36 of the support. This would make the connection with the electrical generator easier. However, an electrical connection with the electrically conductive elements of the wires may be more difficult to establish.

In some embodiments, such as represented in FIG. 11, the wires 20 may be used as a support for an electrically conductive web 70 electrically connected with the electrical conductor. The use of an electrically conductive web as an electrically conductive element advantageously increases the efficiency of the electroporation.

Especially in this embodiment, the wires 20 may not be electrically conductive, provided that there is an electrical connection between the web 70 and the electrical conductor, in particular the cable 60. The web 70 is preferably made of an elastic material encouraging its deployment. The wires 20 may then be arranged so as to tension and stiffen the web 70 in the deployed position.

The insertion part of the electrode device, and in particular the distal part of the support 25, may be provided, on their outer upper and/or bottom surfaces, with electrical contact(s) 71, for instance a coating, electrically connected with the wires. As the provision of conductive webs, this embodiment advantageously increases the useful surface (able to create an electrical field) of the electrode device.

Variations

Many variations of an electrode device of the invention are contemplated.

Figure 8:
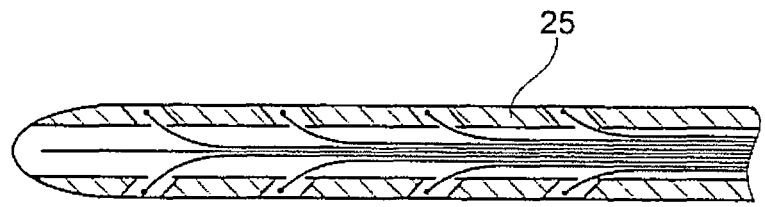
Figure 9:
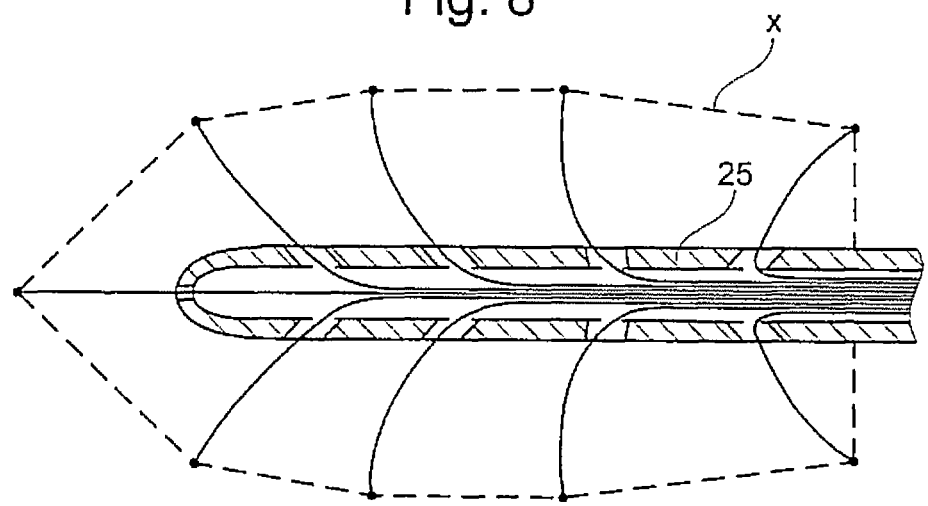

The openings of the support 25 through which the wires 20 protrude in the deployed position are not necessarily positioned at the distal end of the support and may be disposed anywhere on the distal part of support, and in particular on the lateral sides of the distal part of the support 25 (see in particular FIGS. 8 and 9).

Figure 6:
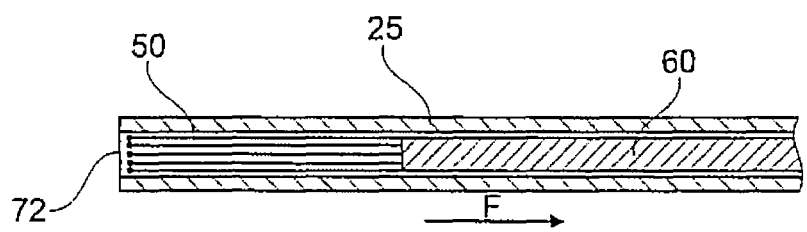
FIGS. 6 to 14 represent different embodiments of the insertion part of an electrode device according to the invention, in a substantially horizontal longitudinal median cross sections, in retracted positions (FIGS. 6, 8, 10) and deployed positions (FIGS. 7, 9, 11, 12, 13 and 14)
Figure 10:
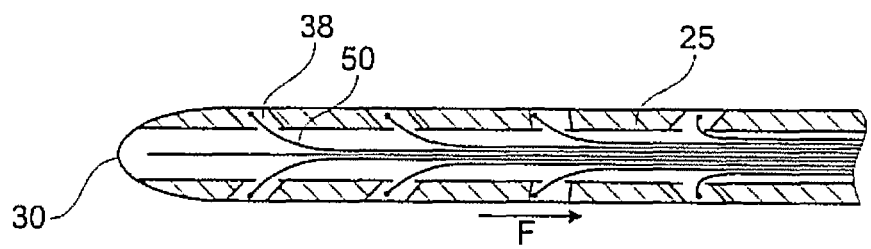

In one embodiment, as represented on FIGS. 6 and 10, the support 25 is a sleeve, slidably mounted on a core, the proximal ends of the wires being fixed to the distal end of the core.

The core may be a cable 60, as previously described.

A pull on the support 25 (arrow F), makes the wires 20 exit from their respective openings, i.e. from an axial opening 72 in FIG. 6 and from lateral openings in FIG. 10. Advantageously, in the service position, the deployment of the wires 20 does not impart any movement of the wires frontwards. The risk of damaging the eye is therefore reduced.

Also with a sliding support, the distal end of the support 25 may be rounded off so as to make easier the introduction of the electrode device toward the service position, as represented in FIG. 10.

Figure 12:
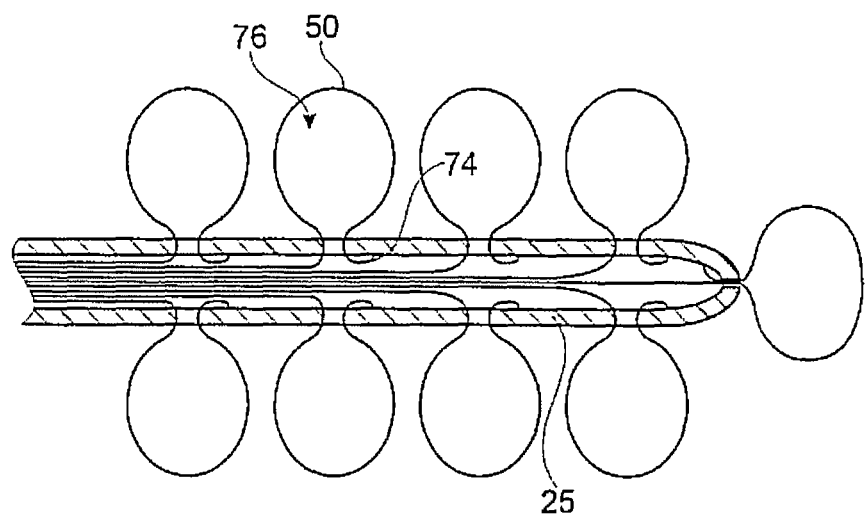

In one embodiment, as represented in FIG. 12, the distal end of a wire 20 may not project from the support 25. Indeed, the distal end 74 of a wire may be fixed to the support, for instance inside the support 25, so that, when the wire 20 is pushed toward the distal tip 30 (or equivalently when the support 25, acting as a sliding sleeve, is pulled toward the proximal end of the electrode device), the wire 20 is pushed away from the support 25 in the shape of a loop 76. Advantageously, the deployment of a loop limits the risk of damaging the eye.

The dimensions and the number of the electrically conductive elements is not limited, provided that the electrical conductor enables, in said deployed position, an electrical connection between said electrically conductive element(s) and an electrical generator. Preferably, the set of electrically conductive elements extends along at least two dimensions. For instance, it comprises at least two wires, or it comprises at least a conductive web.

Figure 13:
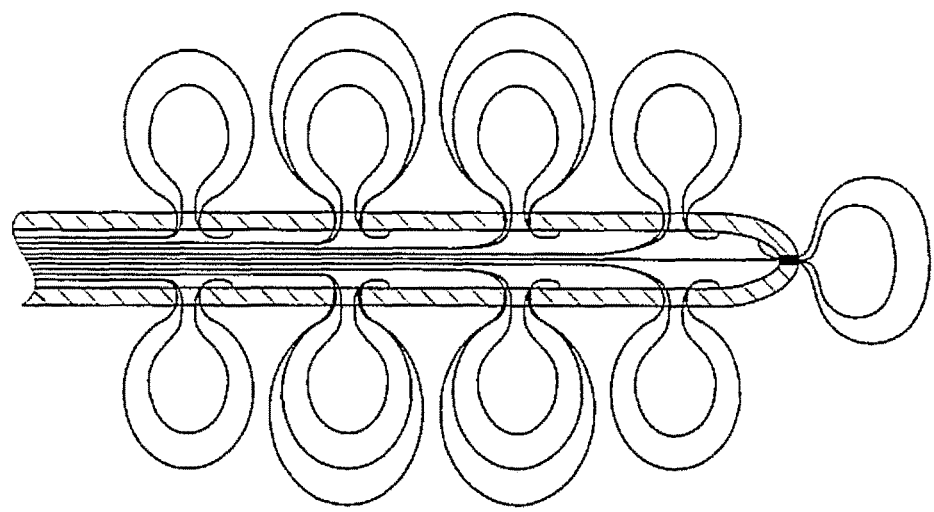

Of course, the characteristics of the different embodiments may be combined. For instance, the same electrode device may comprise, in the deployed position, loops 76, as represented in FIG. 12 or 13, and curved line wires, as represented in the other embodiments. The electrode device may also comprise one or several loops 76 and a support in the shape of a sliding sleeve adapted so as to deploy said loop(s).

Figure 14:
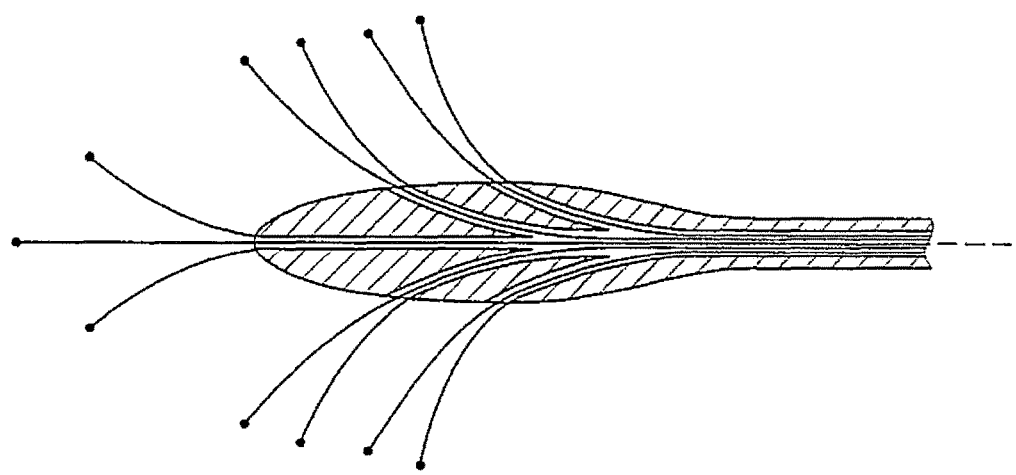

The number of wires 20 exiting from the same opening is not limited, as represented in FIGS. 13 and 14.

Electroporation Device

An electroporation device according to the invention is represented in FIG. 1. It comprises an electrode device 10 according to the invention, a counter electrode 80, in the shape of a surface electrode, and an electrical generator 26 so as to polarize differently the wires 20 of the electrode device according to the invention and the counter electrode 80. This polarization creates an electrical field E between the wires of the electrode device of the invention and the counter electrode.

The counter electrode 80 may be a plate electrode, preferably made of a rigid material, applied on the outside surface of the eye. The counter electrode may be, for instance, a wire type electrode or a plate contact type electrode. Preferably, the counter electrode is curved, preferably spherically, the radius of curvature being preferably greater than 9 mm, greater than 10 mm or greater than 11 mm, and/or less than 15 mm, less than 14 mm, less than 13 mm, or less than 12 mm.

The counter electrode is optionally adapted to be reversibly applied on the surface of the eye.

The counter electrode is preferably made of a conductive non oxidative metal selected for example from iridium, platinum, iridium/platinum, and gold, or made of carbon, stainless steel, silver, aluminium, tungsten . . . .

The electrical generator 26 is adapted so as to generate an electrical field enabling electroporation, as described hereafter for instance.

According to the invention, all the wires 20 which are electrically connected to the electrical generator 26 have the same polarity. Preferably, all the wires are electrically connected together. However, in one embodiment, some of the wires 20 may not be electrically connected to the electrical generator 26.

In one embodiment, the number of wires 20 which are electrically connected together may be changed by the operator.

In one embodiment, the operator may change the wires 20 which are electrically connected to the electrical generator. It becomes therefore possible to change the shape of the electrical field E.

Pharmaceutical Composition

An electroporation device according to the invention may be used for the electroporation of a therapeutic nucleic acid of interest after delivering a pharmaceutical composition formulated with said therapeutic nucleic acid into the suprachoroidal space of a diseased eye.

The nucleic acid to be used in the instant invention can be any nucleic acid of interest exhibiting a biological property. More particularly, the nucleic acid can be any nucleic acid encoding a natural, truncated, artificial, chimeric or recombinant product [e.g., a polypeptide of interest (including a protein or a peptide), a RNA, etc.] exhibiting a biological activity.

The nucleic acid is preferably a desoxyribonucleic acid (DNA) molecule (cDNA, gDNA, synthetic DNA, artificial DNA, recombinant DNA, etc.) or a ribonucleic acid (RNA) molecule (mRNA, tRNA, RNAi, RNAsi, catalytic RNA, antisens RNA, viral RNA, etc.). The nucleic acid may be single stranded or multiple stranded nucleic acid, preferably double-stranded nucleic acid or may be complexed. The nucleic acid may comprise hybrid sequences or synthetic or semi-synthetic sequences. It may be obtained by any technique known to persons skilled in the art, and especially by screening libraries, by chemical synthesis, or alternatively by mixed methods including chemical or enzymatic modification of sequences obtained by screening libraries.

In a particular embodiment, the therapeutic nucleic acid is of synthetic or biosynthetic origin, or extracted from a virus or from a unicellular or pericellular eukaryotic or prokaryotic organism.

The therapeutic nucleic acid used in the present invention may be naked, may be complexed to any chemical, biochemical or biological agent, may be inserted in a vector, etc., when administered to the suprachoroidal space.

As used herein, the term "naked DNA" refers to any nucleic acid molecule which is not combined to a synthetic, biosynthetic, chemical, biochemical or biological agent improving the delivery or transfer of said DNA, or facilitating its entry into the cell.

As used herein, the term "vector" refers to a nucleic acid molecule capable of transporting another nucleic acid to which it has been linked. This term also refers in the present application to any delivery carrier, such as a composition associated to a therapeutic or prophylactic nucleic acid in order to increase its cellular delivery.

Preferred vectors are those capable of autonomous replication and/or expression of nucleic acids to which they are linked Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form, are not bound to the chromosome. In the present invention, the plasmid is the most commonly used form of vector. The plasmid is a preferred form of naked DNA according to the invention.

Vectors may also be episomal DNA, yeast artificial chromosomes, minichromosomes or viral vectors wherein the viral vector is selected from the group consisting of a lentivirus, an adenovirus, an adeno-associated virus and a virus-like vector.

The vector may also be a lipid vesicle such as a liposome. Lipid based compounds which are not liposomes may further be used. For example, lipofectins and cytofectins are lipid-based positive ions that bind to negatively charged nucleic acid and form a complex that can ferry the DNA across a cell membrane. The invention is intended to include such other forms of expression vectors which serve equivalent functions and which become known in the art subsequently hereto.

In addition, the nucleic acid according to the invention may also contain one or more additional regions, for example regulatory elements of small or large size which are available to the skilled artisan such as a promoter region (constitutive, regulated, inducible, tissue-specific, etc.), for example sequences allowing and/or promoting expression in the targeted tissue (e.g. choroid or retina) or cells (e.g. RPE or photoreceptors), a transcription termination signal, secretion sequences, an origin of replication and/or nuclear localization signal (nls) sequences which further enhance polynucleotide transfer to the cell nucleus. Such nls sequences have been described in the prior art including the SV40 large T antigen sequence.

Additionally, the nucleic acid may further comprise selectable markers useful in selecting, measuring, and monitoring nucleic acid transfer results (transfer to which tissues, duration of expression, etc.). The types of expression systems and reporter genes that can be used or adapted for use are well known in the art. For example, genes coding for a luciferase activity, an alkaline phosphatase activity, or a green fluorescent protein activity are commonly used.

The nucleic acid according to the invention may contain any nucleotide sequence of any size. The nucleic acid may thus vary in size from a simple oligonucleotide to a larger molecule such as a nucleotide sequence including exons and/or introns and/or regulatory elements of any sizes (small or large), a gene of any size, for example of large size, or a chromosome for instance, and may be a plasmid, an episome, a viral genome, a phage, a yeast artificial chromosome, a minichromosome, an antisense molecule, etc.

In a particularly preferred embodiment, the polynucleotide is a double-stranded, circular DNA, such as a plasmid, encoding a product with biological activity.

The nucleic acid can be prepared and produced according to conventional recombinant DNA techniques, such as amplification, culture in prokaryotic or eukaryotic host cells, purification, etc. The techniques of recombinant DNA technology are known to those of ordinary skill in the art.

In a particular embodiment, the nucleic acid of interest is capable of exerting a beneficial effect on the targeted cells. It may compensate for a deficiency in or reduce an excess of an endogenous substance. Alternatively, it may confer new properties on the targeted cells. It may be for example an antisense sequence or nucleic acid encoding a polypeptide which can affect the function, morphology, activity and/or metabolism of ocular cells.

The down regulation of gene expression using antisense nucleic acids can be achieved at the translational or transcriptional level. Antisense nucleic acids of the invention are preferably nucleic acid fragments capable of specifically hybridizing with a nucleic acid encoding an endogenous ocular active substance or the corresponding messenger RNA. These antisense nucleic acids can be synthetic oligonucleotides, optionally modified to improve their stability and selectivity. They can also be DNA sequences whose expression in the cell produces RNA complementary to all or part of the mRNA encoding an endogenous ocular active substance. Antisense nucleic acids can be prepared by expression of all or part of a nucleic acid encoding an endogenous ocular active substance, in the opposite orientation. Any length of antisense sequence is suitable for practice of the invention so long as it is capable of down-regulating or blocking expression of the endogenous ocular active substance. Preferably, the antisense sequence is at least 20 nucleotides in length. The preparation and use of antisense nucleic acids, DNA encoding antisense RNAs and the use of oligo and genetic antisense is disclosed in WO92/15680, the content of which is incorporated herein by reference.

Among the biologically active polypeptides or proteins optionally expressed by a nucleic acid as described above and suitable for practice of the invention are enzymes, blood derivatives, hormones, lymphokines, cytokines, chimiokines, anti-inflammatory factors, growth factors, trophic factors, neurotrophic factors, haematopoietic factors, angiogenic factors, anti-angiogenic factors, inhibitors of metalloproteinase, regulators of apoptosis, coagulation factors, receptors thereof, in particular soluble receptors, a peptide which is an agonist or antagonist of a receptor or of an adhesion protein, antigens, antibodies, fragments or derivatives thereof and other essential constituents of the cell, proteins involved in the visual cycle within RPE cells, and structure proteins of retinal cells.

Various retina-derived neurotrophic factors have the potential to rescue degenerating photoreceptor cells, and may be delivered through a method according to the present invention. Preferred biologically active agents may be selected from VEGF, Angiogenin, Angiopoietin-1, DeM, acidic or basic Fibroblast Growth Factors (aFGF and bFGF), FGF-2, Follistatin, Granulocyte Colony-Stimulating factor (G-CSF), Hepatocyte Growth Factor (HGF), Scatter Factor (SF), Leptin, Midkine, Placental Growth Factor (PGF), Platelet-Derived Endothelial Cell Growth Factor (PD-ECGF), Platelet-Derived Growth Factor-BB (PDGF-BB), Pleiotrophin (PTN), RdCVF (Rod-derived Cone Viability Factor), Progranulin, Proliferin, Transforming Growth Factor-alpha (TGF-alpha), Transforming Growth Factor-beta (TGF-beta), Tumor Necrosis Factor-alpha (TNF-alpha), Vascular Endothelial Growth Factor (VEGF), Vascular Permeability Factor (VPF), CNTF, BDNF, GDNF, PEDF, NT3, BFGF, angiopoietin, ephrin, EPO, NGF, IGF, GMF, aFGF, NT5, Gax, a growth hormone, [alpha]-1-antitrypsin, calcitonin, leptin, an apolipoprotein, an enzyme for the biosynthesis of vitamins, hormones or neuromediators, chemokines, cytokines such as IL-1, IL-8, IL-10, IL-12, IL-13, a receptor thereof, an antibody blocking anyone of said receptors, TIMP such as TIMP-1, TIMP-2, TIMP-3, TIMP-4, angioarrestin, endostatin such as endostatin XVIII and endostatin XV, ATF, angiostatin, a fusion protein of endostatin and angiostatin, the C-terminal hemopexin domain of matrix metalloproteinase-2, the kringle 5 domain of human plasminogen, a fusion protein of endostatin and the kringle 5 domain of human plasminogen, the placental ribonuclease inhibitor, the plasminogen activator inhibitor, the Platelet Factor-4 (PF4), a prolactin fragment, the Proliferin-Related Protein (PRP), the antiangiogenic antithrombin III, the Cartilage-Derived Inhibitor (CDI), a CD59 complement fragment, vasculostatin, vasostatin (calreticulin fragment), thrombospondin, fibronectin, in particular fibronectin fragment gro-beta, an heparinase, human chorionic gonadotropin (hCG), interferon alpha/beta/gamma, interferon inducible protein (IP-10), the monokine-induced by interferon-gamma (Mig), the interferon-alpha inducible protein 10 (IP10), a fusion protein of Mig and IP10, soluble Fms-Like Tyrosine kinase 1 (FLT-1) receptor, Kinase insert Domain Receptor (KDR), regulators of apoptosis such as Bcl-2, Bad, Bak, Bax, Bik, Bcl-X short iso form and Gax, fragments or derivatives thereof and the like.

In a particular embodiment, the nucleic acid encodes a soluble fragment of the TNF[alpha] receptor, the TGF [beta]2 receptor, of VEGFR-1, VEGFR-2, VEGFR-3, CCR2 or MIP1. The nucleic acid may also, in another preferred embodiment, encode an antibody, a variable fragment of a single-chain antibody (ScFv) or any other antibody fragment having recognition capacities for the purposes of immunotherapy.

In a particular embodiment of the present invention, the biologically active nucleic acid encodes a precursor of a therapeutic protein usable in the present invention such as those described above.

In another particular embodiment, the electroporation device of the invention is particularly suitable for performing gene replacement. Accordingly the nucleic acid may encode for a viable protein so as to replace the defective protein which is naturally expressed in the targeted tissue. Typically, defective genes that may be replaced include but are not limited to genes that are responsible for retinal degenerative diseases such as retinitis pigmentosa (RP), Leber congenital amaurosis (LCA), recessive RP, Dominant retinitis pigmentosa, X-linked retinitis pigmentosa, Incomplete X-linked retinitis pigmentosa, dominant, Dominant Leber congenital amaurosis, Recessive ataxia, posterior column with retinitis pigmentosa, Recessive retinitis pigmentosa with para-arteriolar preservation of the RPE, Retinitis pigmentosa RP12, Usher syndrome, Dominant retinitis pigmentosa with sensorineural deafness, Recessive retinitis punctata albescens, Recessive Alström syndrome, Recessive Bardet-Biedl syndrome, Dominant spinocerebellar ataxia w/macular dystrophy or retinal degeneration, Recessive abetalipoproteinemia, Recessive retinitis pigmentosa with macular degeneration, Recessive Refsum disease, adult form, Recessive Refsum disease, infantile form, Recessive enhanced S-cone syndrome, Retinitis pigmentosa with mental retardation, Retinitis pigmentosa with myopathy, Recessive Newfoundland rod-cone dystrophy, Retinitis pigmentosa sinpigmento, Sector retinitis pigmentosa, Regional retinitis pigmentosa, Senior-Loken syndrome, Joubert syndrome, Stargardt disease, juvenile, Stargardt disease, late onset, Dominant macular dystrophy, Stargardt type, Dominant Stargardt-like macular dystrophy, Recessive macular dystrophy, Recessive fundus flavimaculatus, Recessive cone-rod dystrophy, X-linked progressive cone-rod dystrophy, Dominant cone-rod dystrophy, Cone-rod dystrophy; de Grouchy syndrome, Dominant cone dystrophy, X-linked cone dystrophy, Recessive cone dystrophy, Recessive cone dystrophy with supernormal rod electroretinogram, X-linked atrophic macular dystrophy, X-linked retinoschisis, Dominant macular dystrophy, Dominant radial, macular drusen, Dominant macular dystrophy, bull's-eye, Dominant macular dystrophy, butterfly-shaped, Dominant adult vitelliform macular dystrophy, Dominant macular dystrophy, North Carolina type, Dominant retinal-cone dystrophy 1, Dominant macular dystrophy, cystoid, Dominant macular dystrophy, atypical vitelliform, Foveomacular atrophy, Dominant macular dystrophy, Best type, Dominant macular dystrophy, North Carolina-like with progressive, Recessive macular dystrophy, juvenile with hypotrichosis, Recessive foveal hypoplasia and anterior segment dysgenesis, Recessive delayed cone adaptation, Macular dystrophy in blue cone monochromasy, Macular pattern dystrophy with type II diabetes and deafness, Flecked Retina of Kandori, Pattern Dystrophy, Dominant Stickler syndrome, Dominant Marshall syndrome, Dominant vitreoretinal degeneration, Dominant familial exudative vitreoretinopathy, Dominant vitreoretinochoroidopathy; Dominant neovascular inflammatory vitreoretinopathy, Goldmann-Favre syndrome, Recessive achromatopsia, Dominant tritanopia, Recessive rod monochromacy, Congenital red-green deficiency, Deuteranopia, Protanopia, Deuteranomaly, Protanomaly, Recessive Oguchi disease, Dominant macular dystrophy, late onset, Recessive gyrate atrophy, Dominant atrophia greata, Dominant central areolar choroidal dystrophy, X-linked choroideremia, Choroidal atrophy, Central areolar, Central, Peripapillary, Dominant progressive bifocal chorioretinal atrophy, Progresive bifocal Choroioretinal atrophy, Dominant Doyne honeycomb retinal degeneration (Malattia Leventinese), Amelogenesis imperfecta, Recessive Bietti crystalline corneoretinal dystrophy, Dominant hereditary vascular retinopathy with Raynaud phenomenon and migraine, Dominant Wagner disease and erosive vitreoretinopathy, Recessive microphthalmos and retinal disease syndrome; Recessive nanophthalmos, Recessive retardation, spasticity and retinal degeneration, Recessive Bothnia dystrophy, Recessive pseudoxanthoma elasticum, Dominant pseudoxanthoma elasticum; Recessive Batten disease (ceroid-lipofuscinosis), juvenile, Dominant Alagille syndrome, McKusick-Kaufman syndrome, hypoprebetalipoproteinemia, acanthocytosis, palladial degeneration; Recessive Hallervorden-Spatz syndrome; Dominant Sorsby's fundus dystrophy, Oregon eye disease, Kearns-Sayre syndrome, Retinitis pigmentosa with developmental and neurological abnormalities, Basseb Korenzweig Syndrome, Hurler disease, Sanfilippo disease, Scieie disease, Melanoma associated retinopathy, Sheen retinal dystrophy, Duchenne macular dystrophy, Becker macular dystrophy, and Birdshot Retinochoroidopathy. Examples of genes include but are not limited to genes encoding for ATP-binding cassette transporter, RPE65, RdCVF, CP290 . . . .

In another embodiment, the electroporation device of the invention is particularly suitable for performing exon skipping for restoring the function of mutated proteins responsible for retinal degenerative disease. Exon skipping involves blocking or preventing the incorporation into mature mRNA of one or more targeted exon(s) which encodes amino sequences that are responsible for a protein dysfunction. This is accomplished by exposing the pre-mRNA that includes exons encoding the protein to antisense oligonucleotides (AONs) which are complementary to sequence motifs that are required for correct splicing of the one or more targeted exons. The AONs bind to complementary required sequences in the pre-mRNA and prevent normal splicing. Instead, the targeted exons are excised and are not included in the mature mRNA that is translated into protein, and the amino acid sequences encoded by the targeted exons are missing from the translated protein.

Furthermore, in another embodiment of the present invention, a mixture of nucleic acids encoding distinct biologically active products can be used. This variant allows co-expression of different products in the ocular cells.

The pharmaceutical composition of the invention may also comprise compatible or physiologically acceptable carrier, excipient or diluent.

The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Pharmaceutically compatible or physiologically acceptable carrier, excipient or diluent includes diluents and fillers which are pharmaceutically acceptable for the methods of the invention, are sterile, and may be selected from neutral to slightly acidic, isotonic, buffered saline (including phosphates, chloride, etc.), aqueous or oleaginous solutions or suspensions and more preferably from sucrose, trehalose, surfactants, proteins and amino acids. The pharmaceutically compatible or physiologically acceptable carrier, excipient or diluent is preferably formulated using suitable dispersing, wetting, suspending, soothing, isotonic or viscosity building agents, stabilizers, preservatives and appropriate buffer to form an isotonic solution. The particular pharmaceutically acceptable carrier and the ratio of active compound to carrier are determined by the solubility and chemical properties of the composition, the particular mode of administration, and standard pharmaceutical practice. Those skilled in the art will understand how to formulate such vehicles by known techniques.

An example of stabilizers is disodium edetate or the like. Examples of isotonic agents are glycerin, propylene glycol, polyethylene glycol, sodium chloride, potassium chloride, sorbitol and mannitol or the like. Examples of buffers are citric acid, sodium hydrogenphosphate, glacial acetic acid and trometamol or the like. Examples of pH adjusters are hydrochloric acid, citric acid, phosphoric acid, acetic acid, sodium hydroxide, sodium carbonate and sodium hydrogencarbonate or the like. An example of soothing agents is benzyl alcohol or the like. Examples of preservatives are benzalkonium chloride, benzethonium chloride, p-hydroxybenzoate esters, sodium benzoate and chlorobutanol or the like.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from about 0.01 to about 2 wt. %.

Preparation forms of the pharmaceutical composition intended for administration to suprachoroidal space are preferably liquid preparations. The liquid preparations can be prepared, for example, by dissolving the biologically active agent in BSS (Balanced Salt Solution), a glycerin solution, a hyaluronic acid solution and the like. A particular composition comprises for example BBS (60%) and hyaluronic acid (40%). A stabilizer, an isotonic agent, a buffer, a pH adjustor, a soothing agent, a preservative, electrolytes, such as sodium, potassium, calcium, magnesium and/or chloride or the like can optionally be added in an adequate amount to the liquid preparations.

The pharmaceutical composition may comprise or the biologically active agent may be combined (in a use according to the present invention) with any additional active ingredient or adjuvant. The adjuvant may be selected from any substance, mixture, solute or composition facilitating or increasing the biological activity of the prophylactic or therapeutic agent such as any biologic, synthetic or biosynthetic agent which improves the delivery or transfer of said agent and may be assimilated to a vector (as delivery carrier) according to the invention. The adjuvant may be conditioned and administered separately or sequentially from the prophylactic or therapeutic agent containing composition and/or at a distinct site of injection. Treatment with multiple agents and/or adjuvants according to the invention need not be done using a mixture of agents and/or adjuvants but may be done using separate pharmaceutical preparations. The preparations need not be delivered at the same exact time, but may be coordinated to be delivered to a patient during the same period of treatment, i.e., within a week or a month or each other.

Any suitable therapeutic agents can be coordinated with the compositions of the present invention. Non-limiting examples of therapeutic agents which may be administered in addition to the above biologically active (prophylactic or therapeutic) agent(s) through a method according to the present invention also include permeabilizing agents such as a virus, a lipid vesicle, hyaluronic acid, lipid-based positive ions, polycationic emulsions, cationic peptides, polyplex, etc.; Actual dosage levels of active ingredients in the compositions of the present invention may be adapted so as to obtain an amount of active ingredient that is effective to obtain a desired biological activity. It should be understood, however, that the specific dose level for any particular patient will depend upon a variety of factors including the body weight, general health, sex, diet, time, rates of absorption and excretion, combination with other drugs and the severity of the particular disease being treated.

Kit

In accordance with the present invention, kits for preventing or treating an ocular disease are envisioned. An electrode device according to the invention and a pharmaceutical composition according to the present invention, and optionally a counter electrode, optionally an electrical generator, optionally instructions for use may be supplied together in a kit. Within the kit, the components may be separately packaged or contained.

Instructions can be in a written, video, or audio form, can be contained on paper, an electronic medium, or even as a reference to another source, such as a website or reference manual.

Other components such as excipients, carriers, other drugs or adjuvants, instructions for administration of the active substance or composition, and administration or injection devices can be supplied in the kit as well.

Method

According to the invention, a method for treating an ocular disease in a subject may comprise the steps consisting of
i) delivering a pharmaceutical composition formulated with a therapeutic nucleic acid of interest into the suprachoroidal space of the diseased eye and
ii) exposing the region where the pharmaceutical composition was delivered to an electrical field generated with an electroporation device according to the invention.

The pharmaceutical composition is preferably chosen among the pharmaceutical compositions which are described here above.

Diseases

The method of the present invention is particularly suitable for the treatment of ocular diseases affecting the posterior region of the eye, and more particularly ocular diseases affecting the retina. Non-limiting examples of ocular diseases that may be treated by the method of the present invention include ocular diseases affecting the macula such as age related macular degeneration (wet and dry) or inherited macular degeneration, macular oedema of any origin (age related macular degeneration, diabetes, inflammation, degeneration, central serous chorioretinitis or diffuse epitheliopathy . . . ), inherited retinal dystrophies, such as Leber congenital amaurosis, retinitis pigmentosa, cone rod dystrophies, best vitelliforme maculopathy, intraocular inflammation such retinitis, chorioretinitis, choroiditis, ischemic retinopathy (in particular retinopathy of prematurity and diabetic retinopathy), retinal vascular diseases, ocular ischemia syndrome and other vascular anomalies, choroidal disorders and tumors, vitreous disorders, glial proliferation such as proliferative vitreo retinopathy and glial proliferation associated to diabetic pre retinal angiogenesis, diabetic retinopathy ischemic or proliferative.

Inherited retinal dystrophies or retinitis pigmentosa are inherited blinding diseases due to mutations or deletions in gene implicated in the visual cycle. They begin in the young age and progress slowly until total blindness. Loss of photoreceptors is associated to loss of retinal pigment cells and to vascular and optic nerve atrophy at the later stages. Some of these inherited degeneration are due to mutation in mitochondrial DNA. In particular, non limiting examples of retinal degenerative diseases include but are not limited to retinitis pigmentosa (RP), Leber congenital amaurosis (LCA), recessive RP, Dominant retinitis pigmentosa, X-linked retinitis pigmentosa, Incomplete X-linked retinitis pigmentosa, dominant, Dominant Leber congenital amaurosis, Recessive ataxia, posterior column with retinitis pigmentosa, Recessive retinitis pigmentosa with para-arteriolar preservation of the RPE, Retinitis pigmentosa RP12, Usher syndrome, Dominant retinitis pigmentosa with sensorineural deafness, Recessive retinitis *punctata albescens*, Recessive Alström syndrome, Recessive Bardet-Biedl syndrome, Dominant spinocerebellar ataxia w/macular dystrophy or retinal degeneration, Recessive abetalipoproteinemia, Recessive retinitis pigmentosa with macular degeneration, Recessive Refsum disease, adult form, Recessive Refsum disease, infantile form, Recessive enhanced S-cone syndrome, Retinitis pigmentosa with mental retardation, Retinitis pigmentosa with myopathy, Recessive Newfoundland rod-cone dystrophy, Retinitis pigmentosa sinpigmento, Sector retinitis pigmentosa, Regional retinitis pigmentosa, Senior-Loken syndrome, Joubert syndrome, Stargardt disease, juvenile, Stargardt disease, late onset, Dominant macular dystrophy, Stargardt type, Dominant Stargardt-like macular dystrophy, Recessive macular dystrophy, Recessive fundus flavimaculatus, Recessive cone-rod dystrophy, X-linked progressive cone-rod dystrophy, Dominant cone-rod dystrophy, Cone-rod dystrophy; de Grouchy syndrome, Dominant cone dystrophy, X-linked cone dystrophy, Recessive cone dystrophy, Recessive cone dystrophy with supernormal rod electroretinogram, X-linked atrophic macular dystrophy, X-linked retinoschisis, Dominant macular dystrophy, Dominant radial, macular drusen, Dominant macular dystrophy, bull's-eye, Dominant macular dystrophy, butterfly-shaped, Dominant adult vitelliform macular dystrophy, Dominant macular dystrophy, North Carolina type, Dominant retinal-cone dystrophy 1, Dominant macular dystrophy, cystoid, Dominant macular dystrophy, atypical vitelliform, Foveomacular atrophy, Dominant macular dystrophy, Best type, Dominant macular dystrophy, North Carolina-like with progressive, Recessive macular dystrophy, juvenile with hypotrichosis, Recessive foveal hypoplasia and anterior segment dysgenesis, Recessive delayed cone adaptation, Macular dystrophy in blue cone monochromacy, Macular pattern dystrophy with type II diabetes and deafness, Flecked Retina of Kandori, Pattern Dystrophy, Dominant Stickler syndrome, Dominant Marshall syndrome, Dominant vitreoretinal degeneration, Dominant familial exudative vitreoretinopathy, Dominant vitreoretinochoroidopathy; Dominant neovascular inflammatory vitreoretinopathy, Goldmann-Favre syndrome, Recessive achromatopsia, Dominant tritanopia, Recessive rod monochromacy, Congenital red-green deficiency, Deuteranopia, Protanopia, Deuteranomaly, Protanomaly, Recessive Oguchi disease, Dominant macular dystrophy, late onset, Recessive gyrate atrophy, Dominant atrophia greata, Dominant central areolar choroidal dystrophy, X-linked choroideremia, Choroidal atrophy, Central areolar, Central, Peripapillary, Dominant progressive bifocal chorioretinal atrophy, Progresive bifocal Choroioretinal atrophy, Dominant Doyne honeycomb retinal degeneration (Malattia Leventinese), Amelogenesis imperfecta, Recessive Bietti crystalline corneoretinal dystrophy, Dominant hereditary vascular retinopathy with Raynaud phenomenon and migraine, Dominant Wagner disease and erosive vitreoretinopathy, Recessive microphthalmos and retinal disease syndrome; Recessive nanophthalmos, Recessive retardation, spasticity and retinal degeneration, Recessive Bothnia dystrophy, Recessive pseudoxanthoma elasticum, Dominant pseudoxanthoma elasticum; Recessive Batten disease (ceroid-lipofuscinosis), juvenile, Dominant Alagille syndrome, McKusick-Kaufman syndrome, hypoprebetalipoproteinemia, acanthocytosis, palladial degeneration; Recessive Hallervorden-Spatz syndrome; Dominant Sorsby's fundus dystrophy, Oregon eye disease, Kearns-Sayre syndrome, Retinitis pigmentosa with developmental and neurological abnormalities, Basseb Korenzweig Syndrome, Hurler disease, Sanfilippo disease, Scieie disease, Melanoma associated retinopathy, Sheen retinal dystrophy, Duchenne macular dystrophy, Becker macular dystrophy, and Birdshot Retinochoroidopathy.

Intraocular inflammation regroups all types of inflammation of the intraocular tissues, mainly uvea and retina. Intraocular inflammations may be from immunologic causes, infectious causes, iatrogenic causes or of unknown etiologies. They may be acute, recurrent or chronic. Intraocular inflammations are among the most causes of curable blindness. Posterior segment intraocular inflammations may be associated to vasculitis, optic neuritis, vitritis and chorio retinitis, retinitis, choriditis, choroidal neovascularisation, choroidal neovascularization due to AMD, to myopia, inflammation, diffuse epitheliopathy, bruch membrane rupture, polypoidal choroidal vasculopathy, post traumatic . . . .

There are two major types of glaucoma: chronic glaucoma or primary open-angle glaucoma (POAG) and acute closed-angle glaucoma. Other variations include congenital glaucoma, pigmentary glaucoma, neovascular glaucoma and secondary glaucoma. Glaucoma is similar to ocular hypertension but with accompanying optic nerve damage and vision loss. Glaucoma is usually treated with eye drops, laser, or conventional eye surgery. If not treated, glaucoma will cause blindness.

Angiogenesis is the formation of new capillary blood vessels leading to neovascularization. Angiogenesis is a complex process which includes a series of sequential steps including endothelial cell mediated degradation of vascular basement membrane and interstitial matrices, migration of endothelial cells, proliferation of endothelial cells, and formation of capillary loops by endothelial cells. Though angiogenesis is a normal process for the development or maintenance of the vasculature, pathological conditions (i.e., angiogenesis dependent diseases) arise where blood vessel growth is actually harmful. Angiogenesis is notably associated with important diseases of ocular tissue, including diabetic retinopathies, age related macular degeneration, retinopathy of prematurity, corneal graft rejection, neovascular glaucoma and corneal scaring. Any abnormal growth of blood vessels in the eye can scatter and block the incident light prior to reaching the retina. Neovascularization can occur at almost any site in the eye and significantly alter ocular tissue function. Some of the most threatening ocular neovascular diseases are those which involve the retina. For example, many diabetic patients develop a retinopathy which is characterized by the formation of leaky, new blood vessels on the anterior surface of the retina and in the vitreous causing proliferative vitreoretinopathy. A subset of patients with age related macular degeneration develop subretinal neovascularization which leads to their eventual blindness.

Diabetic Retinopathy occurs when the retinal vessels inside the eye leak blood and fluids into the surrounding tissue. About 80% of patient with diabetes develop diabetic retinopathy. This disease is generally treated using a laser. However, laser therapy involves complications including retinal vein occlusion, loss of visual acuity, vitreous hemorrhage and sometimes fails. If left untreated, diabetic retinopathy may cause blindness.

Retinopathy of Prematurity (ROP) affects prematurely born babies. It consists of the abnormal growth of blood vessels within the retinal and vitreous. Progression to later stages of ROP can lead to the formation of scar tissue on the retina, vitreous hemorrhage, and retinal detachment. The treatment is usually performed either by laser or cryotherapy (freezing).

Ischemic retinopathies are retinopathies associated to vascular occlusion (capillaries or large vessels) that lead to neuroretinal suffering, cell death and neo angiogenesis. Macular degeneration is a disease that affects central vision and leads to loss of vision. Although there are forms of macular degeneration that strike young people, the condition occurs most commonly in people who are over 60 years of age. This disorder is thus called age-related macular degeneration (AMD). Because only the center of a person's vision is usually affected, blindness rarely occurs from the disease. However, injury to the macula in the center of the retina can destroy the ability to see straight ahead clearly. Dry forms associate degeneration of neuroretina, RPE cells and choroids. Wet forms associate previously described phenomenons and growth of neovessels from the choriocapillaries and/or retinal vessels, sub retinal detachment and hemorrhages, sub epithelial hemorrhages and tears, etc. Macular degeneration usually occurs after the age of sixty. While your central vision is reduced, most patients retain some vision and never go totally blind.

A particular aspect of the invention is a method of treating intraocular neovessels or macular oedema comprising delivering to the suprachoroidal space of a subject suffering therefrom a nucleic acid encoding an anti VEGF, an anti VEGF receptor or an anti PLGF.

A further particular aspect of the invention is a method of treating or delaying retinitis pigmentosa comprising delivering to the suprachoroidal space of a subject suffering therefrom a nucleic acid encoding a neurotrophic factor as described above.

Another particular aspect of the invention is a method of treating diabetic retinopathy comprising delivering to the suprachoroidal space of a subject suffering therefrom a nucleic acid encoding a nucleic acid encoding an anti IRS-1 or IGF-1.

Operation

A step i), an operator, for instance a physician, injects a pharmaceutical composition into the suprachoroidal space I.

The pharmaceutical composition of the invention may be delivered into the suprachoroidal space at multiple injection sites. The delivering may also be repeated over time.

The means to inject the pharmaceutical composition into the suprachoroidal space may be an injection needle or preferably a flexible catheter or microcannula. Methods for injecting a pharmaceutical injection into the suprachoroidal space are well known in the art (e.g. Einmahl S. Invest Ophtamol Vis Sci 2001 42:695: Galimova V U. Vestn Oftalmo 2001 117:20; Olsen T W Am J. Ophtalmol 2006 142:777). Devices for injecting a pharmaceutical composition into the suprachoroidal space are also well known in the art (e.g. Olsen T W Am J. Ophtalmol 2006 142:777, US 2010173866, WO 2007100745 and WO 2011053512).

The physician then makes a micro-incision M through the sclera S at an appropriate place. He then takes an electrode device of the invention, the set of wires being in the retracted position. The set of wires 20 are supported and protected by the support 25, at least in the distal part of the support to be inserted. The wires substantially do not protrude from the support 25 so as to avoid interference with the introduction of the distal part of the support 25. The shape of the distal part of the support makes the insertion part 12 adapted for an insertion into the suprachoroidal space of the eye in the retracted position, so as to reach the service position.

The physician inserts the distal tip of the electrode device 10 into the mini-incision and guides it between the sclera and choroid so as to avoid any additional lesion. The shape and dimensions of the insertion part of the electrode device makes this insertion easier. If the electrode device is provided with an optical fibre enabling the transmission of light from outside the eye to the distal tip 30 (possibly the support itself), the physician may couple this fibre with a light source, outside the eye, and easily localize the distal tip 30 within the suprachoroidal space, which helps him for placing it in the right service position. In the service position, the length $L_{12}$ of the electrode device which is extending in the suprachoroidal space is preferably more than 5 mm, more than 10 mm and/or less than 40 mm, less than 30 mm.

Once the electrode device is in the service position, the physician deploys the set of wires 20.

The deployment and the retraction of the set of wires are operated remotely, from outside the eye. Any actuator known for similar purposes may be used, in particular the actuators used for catheters. For instance, the physician pushes the cable 60, as represented in FIG. 15. He may also manipulate a control handle 16 if available.

The deployment of the wires 20 is facilitated due to the shape of the guiding tubes and/or the shape memory of the wires.

The physician also places the counter electrode 80 in a position adapted so that an electrical field E may be established between the electrode formed by the electrically conductive elements of the outside parts of the wires of the electrode device according to the invention and the counter electrode 80.

In the present invention, when the choroid or retina is targeted, the electrical field is applied after applying the counter electrode on the surface of the sclera at the opposing side where the suprachoroidal injection was performed.

The electrical generator 26 is connected to the terminal 68 of the electrode device and to the counter electrode 80, so that the terminal 68 (and, correspondingly, the electrically conductive elements of the outside parts of wires 20) and the counter electrode 80 have opposite polarities.

Then, the electrical generator generates an appropriate electrical field E in the region where the pharmaceutical composition was delivered, which provokes an electroporation of the injected therapeutic nucleic acid of interest inside the choroid, RPE and retina. Electroporation is indeed suitable for, or increases, permeability of a cell membrane and/or at least a portion of a targeted tissue adjacent to the suprachoroidal space to a biologically active agent such as a nucleic acid. In addition, a brief electric impulse with a given field strength is used to allow transport or migration of agents through the tissue or across cell membranes into cells, by an electrophoretic effect. The technique of electroporation is well known to those of ordinary skill in the art.

However, to date electroporation failed to transfect adult photoreceptor cells when the plasmids were injected either into the ocular cavity or into the sub retinal space.

In the deployed position, the surface of the choroid which is covered by the electrically conductive elements of the outside parts of the wires is advantageously large, which enables the generation of an efficient electrical field.

This surface may be increased if
  the distal part of the support is itself made of an electrically conductive material, or is at least partially covered by such a material (electrical contacts 71), in electrical connection with the electrically conductive elements of the outside parts of the wires or
  the electrically conductive elements of the outside parts of the wires are in contact with an electrically conductive web 70, or
  electrically conductive elements of the wires which do not project from the support in the deployed position and are electrically connected with the electrically conductive elements of the outside parts of the wires may enter into contact with the choroid (FIG. 4*b*) or with the sclera (FIG. 4*c*).

In a particular embodiment, an electrical field constituted by one or more electrical pulse(s) is applied.

The field intensity of which is between about 1 and 600 Volts, preferably 1 and 400 Volts, even more preferably between about 1 and 200 Volts, advantageously between about 10 and 100 Volts, or 15 and 70 Volts.

The total duration of application of the electric field may be between 0.01 millisecond and 1 second, preferably between 0.01 and 500 milliseconds, more preferably between 1 and 500 milliseconds, even more preferably greater than 1 or 10 milliseconds. In a preferred embodiment, the total duration of application of the electric field is between 10 milliseconds and 100 milliseconds and is preferably of 20 milliseconds.

The number of electric pulses applied may be between for example 1 and 100 000. Their frequency may be comprised between 0.1 and 1000 hertz. It is preferably a regular frequency.

Electric pulses may also be delivered in an irregular manner relative to each other, the function describing the intensity of the electric field as a function of the time for one pulse being preferably variable.

Electric pulses may be unipolar or bipolar wave pulses. They may be selected for example from square wave pulses, exponentially decreasing wave pulses, oscillating unipolar wave pulses of limited duration, oscillating bipolar wave pulses of limited duration, or other wave forms. Preferentially, electric pulses comprise square wave pulses or oscillating bipolar wave pulses.

At the end of the electroporation step, the physician shuts the generator down, retracts the wires inside the support, and pulls the insertion part of the electrode device, through the micro-incision M, out of the suprachoroidal space.

As it now clearly appears, the retracted position facilitates the introduction of the insertion part of the electrode device, its guidance to the desired site of the eye to be treated, and its extraction from the suprachoroidal space, whereas the deployed position provides a large electrode surface.

Therefore, an electrode device according to the present invention allows an intervention that is as minimally invasive as possible, and, with the possibility of deploying the set of wires, enables an efficient electroporation.

Throughout this application, various references describe the state of the art to which this invention pertains. The disclosures of these references are hereby incorporated by reference into the present disclosure.

The invention claimed is:

1. An electroporation device for the electroporation of a therapeutic nucleic acid after delivering a pharmaceutical composition formulated with said therapeutic nucleic acid into the suprachoroidal space of a diseased eye, comprising:
  an electrode device having an insertion part conformed to be inserted into said suprachoroidal space of said eye so as to reach a service position located inside said suprachoroidal space, and a handling part for manipulation of the electrode device, said electrode device comprising:
  a support having a distal part;
  a set of a plurality of wires supported by said support and mobile between a retracted position in which said plurality of wires substantially extend along the support, and a deployed position in which outside parts which are respected parts of said plurality of wires project from said distal part of the support into said suprachoroidal space, the distal part of the support being conformed to be inserted into said suprachoroidal space in said retracted position, the outside parts of the plurality of wires being configured to be inserted into said suprachoroidal space in said deployed position;

at least one electrically conductive element forming at least a portion of said outside parts or supported by said outside parts; —an electrical generator;

an electrical conductor enabling, in said deployed position, an electrical connection between said at least one electrically conductive element and the electrical generator;

an actuator actuated by an operator to move the plurality of wires from said retracted position to said deployed position in said service position;

said insertion part having a distal tip conformed so as to be atraumatic;

a surface counter electrode to be applied on an outside surface of the eye; and the electrical generator adapted to polarize differently said at least one electrically conductive element and the counter electrode, and to generate an electrical field enabling electroporation.

2. The electroporation device according to claim 1, in which a length of said outside parts of the plurality of wires is more than 1 mm and less than 15 mm.

3. The electroporation device according to claim 2, in which a length of said outside parts is more than 4 mm and less than 8 mm.

4. The electroporation device according to claim 1, in which said outside parts of the set of a plurality of wires extend, in the deployed position, along a spherical surface, with a radius of curvature greater than 9 mm and less than 15 mm.

5. The electroporation device according to claim 1, in which each of the outside parts of the plurality of wires comprises the at least one electrically conductive element, the electrical conductor enabling, in said deployed position, an electrical connection between said at least one electrically conductive element and said electrical generator.

6. The electroporation device according to claim 1, in which the at least one electrically conductive element of the plurality of wires is constituted by the outside parts of the plurality of wires, or by the plurality of wires, and/or by an electrically conductive coating of said outside parts and/or by an electrically conductive web at least partially supported by said outside parts.

7. The electroporation device according to claim 1, in which the insertion part of the electrode device is curved, a radius of curvature being greater than 9 mm and less than 15 mm.

8. The electroporation device according to claim 1, in which a width and/or a thickness of the insertion part of the electrode device is less than 2.0 mm.

9. The electroporation device according claim 1, in which a width and/or a thickness of the insertion part of the electrode device is less than 0.5 mm.

10. The electroporation device according to claim 1, in which the distal part of the support is provided with a lumen which
   laterally diverges at an approach of a distal end of the support and opens outwardly at said distal end and/or
   divides into a plurality of guiding tubes opening outwardly through respective openings,
said lumen and said plurality of guiding tubes containing, in the retracted position, one or several of said plurality of wires.

11. The electroporation device according to claim 1, in which a diameter of each wire of the plurality of wires is less than 0.5 mm.

12. The electroporation device according to claim 1, which comprises a cable which, in the service position, performs:
   establishing, at least in the deployed position, an electrically conductive path between the electrical generator and the at least one electrically conductive element; and/or
   establishing a mechanical relationship between the set of a plurality of wires and the outside surface of the eye so that an operator may move said set of a plurality of wires from the retracted position to the deployed position.

13. The electroporation device according to claim 1, in which the support is a sleeve, slidably mounted on a cable, so that a pull or a push on the support makes the plurality of wires exit from or enter into the support, and/or in which, in said deployed position, at least one of said plurality of wires projects from said support in a loop shape.

14. A method of treating an ocular disease in a subject in need thereof, comprising:
   delivering a pharmaceutical composition comprising a therapeutic nucleic acid to a diseased eye; and then
   transferring said therapeutic nucleic acid into the suprachoroidal space of said diseased eye by electroporation using the electroporation device as claimed in claim 1.

15. The electroporation device according to claim 1, wherein the plurality of wires are configured to be atraumatic.

16. The electroporation device according to claim 1, in which, in the deployed position, the outside parts of the plurality of wires exit laterally and/or axially from respective openings of the support.

* * * * *